(12) United States Patent  
Jo

(10) Patent No.: US 10,245,372 B2  
(45) Date of Patent: Apr. 2, 2019

(54) CLEANING INSTRUMENT FOR LARGE INTESTINE

(71) Applicant: WONJIN CO., LTD., Hwaseong-si, Gyeonggi-do (KR)

(72) Inventor: Won Jin Jo, Hwaseong-si (KR)

(73) Assignee: WONJIN CO., LTD., Hwaseong-si, Gyeonggi-do (KR)

( * ) Notice: Subject to any disclaimer, the term of this patent is extended or adjusted under 35 U.S.C. 154(b) by 43 days.

(21) Appl. No.: 15/512,756

(22) PCT Filed: Jul. 7, 2015

(86) PCT No.: PCT/KR2015/006998  
§ 371 (c)(1),  
(2) Date: Mar. 20, 2017

(87) PCT Pub. No.: WO2016/108370  
PCT Pub. Date: Jul. 7, 2016

(65) Prior Publication Data  
US 2017/0304526 A1   Oct. 26, 2017

(30) Foreign Application Priority Data  
Dec. 29, 2014   (KR) .................. 10-2014-0191660

(51) Int. Cl.  
*A61M 3/02*     (2006.01)  
*A61M 9/00*     (2006.01)  
*A61M 39/22*    (2006.01)

(52) U.S. Cl.  
CPC ............ *A61M 3/0216* (2014.02); *A61M 3/02* (2013.01); *A61M 3/022* (2014.02); *A61M 3/025* (2013.01); *A61M 3/0279* (2013.01); *A61M 9/00* (2013.01); *A61M 39/22* (2013.01); *A61M 2205/7572* (2013.01); *A61M 2210/1064* (2013.01); *A61M 2210/1067* (2013.01)

(58) Field of Classification Search  
CPC .. A61M 3/0216; A61M 3/022; A61M 3/0279; A61M 39/22  
USPC ......................................................... 604/119  
See application file for complete search history.

(56) References Cited

U.S. PATENT DOCUMENTS

2006/0025729 A1*   2/2006   Leiboff ............... A61M 3/0283  
                                                           604/317

FOREIGN PATENT DOCUMENTS

KR   10-2002-0028506 A   4/2002  
KR   10-2002-0034146 A   5/2002  
(Continued)

*Primary Examiner* — Phillip A Gray  
(74) *Attorney, Agent, or Firm* — Revolution IP, PLLC

(57) ABSTRACT

Disclosed is a colonic irrigator capable of cleansing the inside of the large intestine and removing impacted feces remaining inside the large intestine by spraying a cleansing solution into the large intestine. The colonic irrigator includes a cleansing body 10 having a laid down egg shape, having a spray hole 12 formed at a lifted portion 11 provided on the upper part thereof and having a cleansing solution channel 13 formed therein to communicate with the spray hole 12, and a connector 20 which has a screw part 21 formed at one side thereof so as to be connected to a shower hose 40, is bent at 90 degrees such that the other side is connected to the lower part of the cleansing body 10, and has a cleansing solution channel 23 formed therein to communicate with the cleansing solution channel 13 of the cleansing body 10, where the cleansing body 10 and the connector 20 are integrated.

11 Claims, 6 Drawing Sheets

(56) References Cited

FOREIGN PATENT DOCUMENTS

KR         20-0335719  Y1     12/2003
KR   20-2009-0006020  U       6/2009

\* cited by examiner

CLEANING INSTRUMENT FOR LARGE INTESTINE

CROSS-REFERENCE TO RELATED APPLICATIONS

This application is a national stage application of International Patent Application No. PCT/KR2015/006998 filed on Jul. 7, 2015, which claims priority to Korean Patent Application No. 10-2014-0191660 filed on Dec. 29, 2014, the entire contents of which are incorporated by reference herein.

TECHNICAL FIELD

The present invention relates to a colonic irrigator capable of cleansing the inside of the large intestine and removing impacted feces remaining inside the large intestine by spraying a cleansing solution into the large intestine, and more particularly, to a colonic irrigator configured to be connected to a shower hose and thus conveniently used without any defecation pain when cleansing water is injected.

BACKGROUND

In general, a colonic irrigator indicates a device in which a tube having a length of 5 to 7 cm is inserted into an anus to remove impurities and impacted feces remaining in the large intestine by repeating the injection and discharge of cleansing water with an adequate pressure. Purified or distilled water is used as the cleansing solution of the colonic irrigator, and some of the colonic irrigators can use chemicals, isotonic water, coffee or tap water for the cleansing solution.

The large intestine is an organ that absorbs water and nutrients which were not absorbed in a small intestine and makes feces by carbon dioxide, methane, and other residues generated during fermentation and dissolution processes by bacteria inside the large intestine. The feces are discharged from the large intestine through an anus formed at the end of the large intestine. However, it is not that all feces formed in the large intestine are discharged through the anus; instead, some may reside in the large intestine, which is called impacted feces.

The impacted feces make harmful substances like methane that may be absorbed together with water when water is absorbed in the large intestine, which has harmful effects on a human body. Accordingly, devices named a colonic irrigator have been developed to remove such impacted feces inside the large intestine.

However, most of the conventional colonic irrigators are expensive and have a complicated structure, and they are available in a hospital, causing a lot of expenses to use them. In addition, the nozzle through which cleansing water is injected is designed to be inserted deeply into the large intestine, which generates a pain upon using them.

SUMMARY OF THE DISCLOSURE

The present invention has been made in view of the above-mentioned problems, and provides a colonic irrigator that has a simple structure to save a production cost. The colonic irrigator is configured to be connected to a shower hose such that it is unnecessary to visit a hospital to remove the impacted feces, while removing a pain around a butt upon cleansing the large intestine because a tube inserted into the anus has a short length.

In addition, the present invention provides a colonic irrigator that can be used regardless of the distance between a shower and a toilet.

The present invention provides a colonic irrigator that can be used although the tap water is not potable.

Embodiments of the present invention provide a colonic irrigator which includes a cleansing body having a laid down egg shape, having a spray hole formed at a lifted portion provided on the upper part thereof and having a cleansing solution channel formed therein to communicate with the spray hole, and a connector which has a screw part formed at one side thereof so as to be connected to a shower hose, is bent at 90 degrees such that the other side is connected to the lower part of the cleansing body, and has a cleansing solution channel formed therein to communicate with the cleansing solution channel of the cleansing body, wherein the cleansing body and the connector are integrated.

According to the colonic irrigator of the present invention, a water pressure regulating member may be provided at a side of the cleansing body. The water pressure regulating member includes a cylinder-shaped extension portion extended from a longitudinal end of the cleansing body and having a pressure regulating hole at a side thereof, a pressure regulating channel formed at the extension portion and the cleansing body to connect the cleansing solution channel of the cleansing body and the pressure regulating hole formed at the extension portion, and a silicone band connected to the extension portion and regulating the opening of the pressure regulating hole.

Also, according to the colonic irrigator of the present invention, a filter may be provided inside the entrance of the connector to remove impurities contained in the cleansing solution, and a flow regulating valve may be further provided downstream of the filter to regulate the spraying amount of the cleansing solution by changing an opening of the cleansing solution channel.

The colonic irrigator according to an embodiment of the present invention further includes a hose connection tip having screw parts at opposite ends to connect the shower hose and a connection hose when the shower hose is short.

Also, the colonic irrigator according to an embodiment of the present invention may include a cleansing solution providing member disposed between the shower hose and the connector to supply the cleansing solution to the connector due to the pressure of water provided through the shower hose. The cleansing solution providing member further includes a pressurizing portion which volume expands due to the water provided by the shower hose and a cleansing solution storing portion storing the cleansing solution therein, which volume decreases as the volume of the pressurizing portion expands, such that the cleansing solution is supplied to the connector.

According to the colonic irrigator of the present invention, the pressurizing portion and the cleansing solution providing portion are integrally formed and partitioned by a flexible separating wall disposed in a container having a fixed volume.

The present invention provides the colonic irrigator in which a lifted portion of the cleansing body is only inserted into an anus, thereby minimizing any pains upon using it. Its simple structure also reduces production and maintenance costs. Moreover, since the cleansing body having a laid down egg shape compresses a butt and weakens an inclination for stool, thereby postponing a bowel movement and allowing the cleansing solution to reach deeper into an anus.

The present invention provides the colonic irrigator which can be used conveniently because the pressure of the cleansing solution sprayed through the spray hole is regulated using a simple structure.

The present invention provides the colonic irrigator which can be managed in a sanitary way because impurities contained in the cleansing solution are removed and the spraying amount of the cleansing solution can be regulated.

The present invention provides the colonic irrigator which can be used regardless of the distance between a shower and a toilet, resulting from the connection of the shower hose and the connection hose by using a hose connection tip.

Also, the present invention provides the colonic irrigator which can be used independently of the places by connecting and using a separate cleansing solution providing member when the tap water cannot be used as the cleansing solution.

DETAILED DESCRIPTION OF PREFERRED EMBODIMENTS

Hereinafter, a colonic irrigator according to an embodiment of the present invention will be described in details with reference to accompanying drawings.

Figure 1:
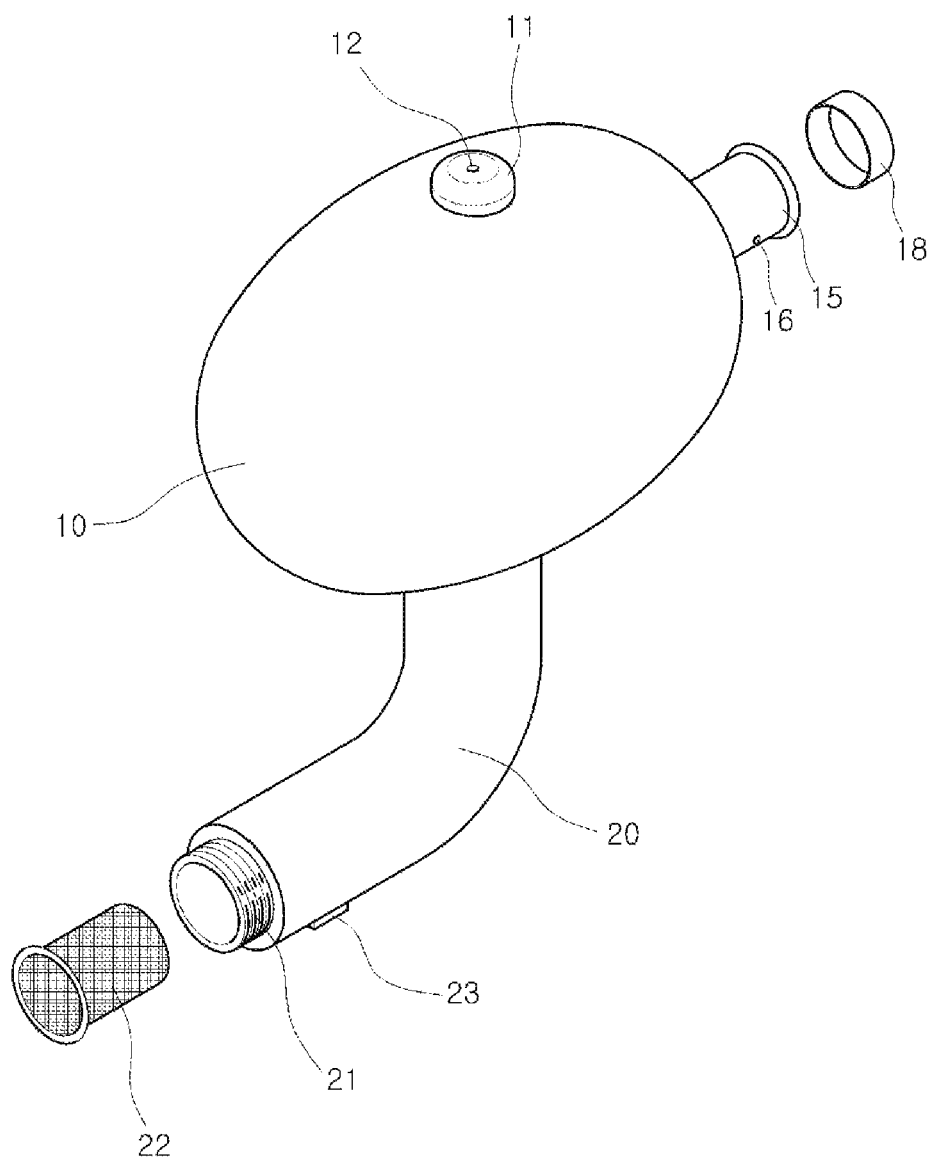
FIG. 1 is a perspective view illustrating an appearance of a colonic irrigator according to an embodiment of the present invention.
Figure 2A:
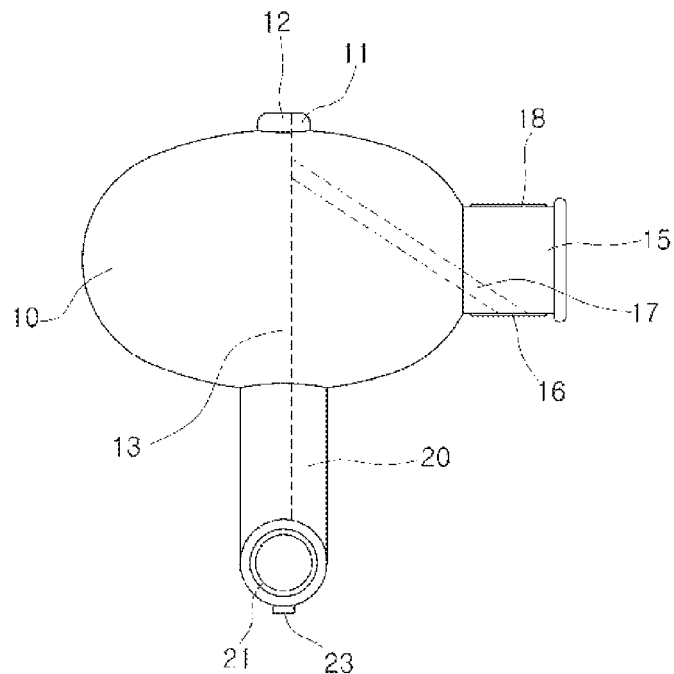
FIG. 2 is a view illustrating an internal structure of a colonic irrigator according to an embodiment of the present invention.
Figure 2B:
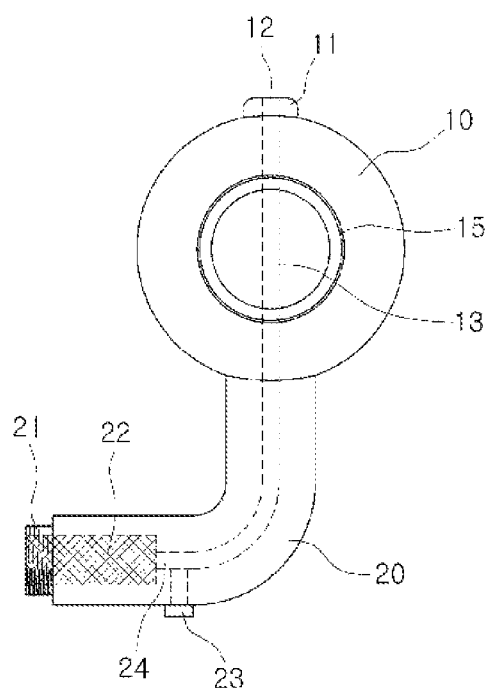
Figure 3:
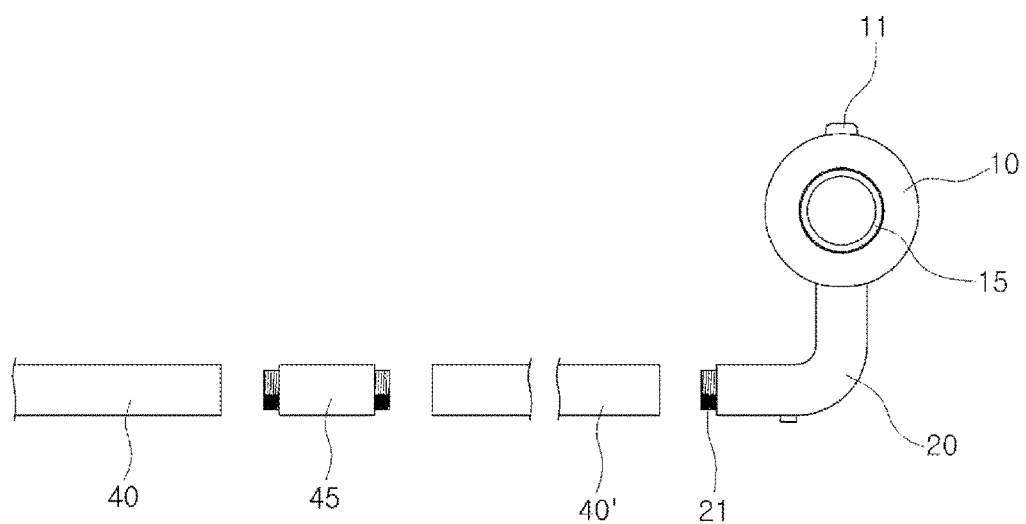
FIG. 3 is a schematic view illustrating an example of a colonic irrigator according to an embodiment of the present invention.
Figure 4:
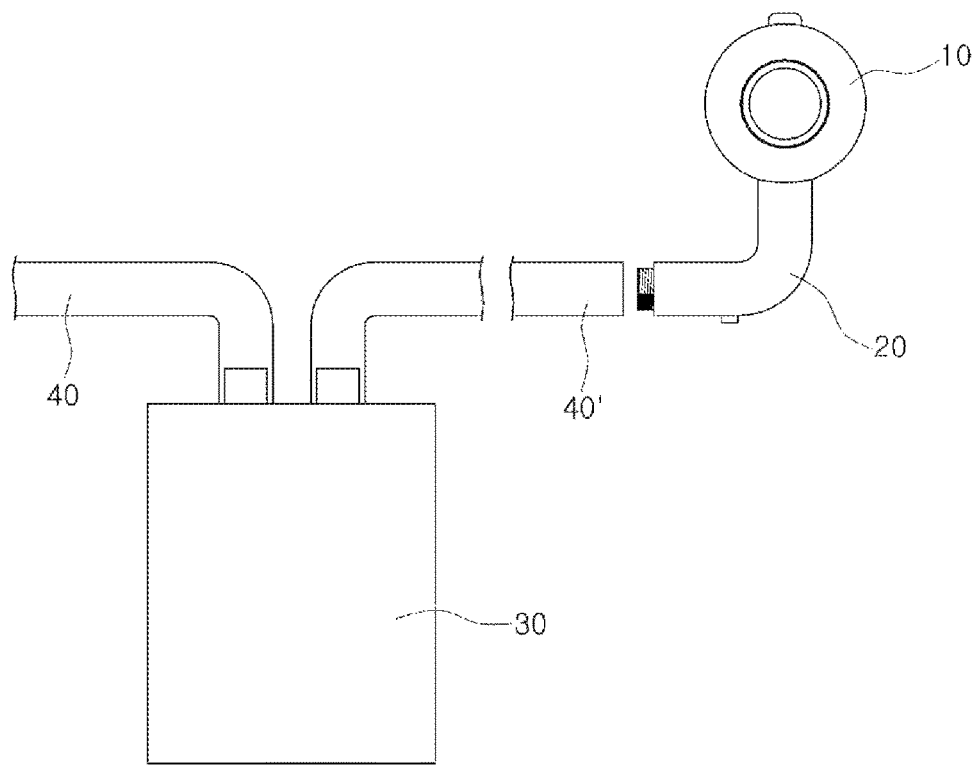
FIG. 4 is a schematic view illustrating another example of a colonic irrigator according to an embodiment of the present invention.
Figure 5:
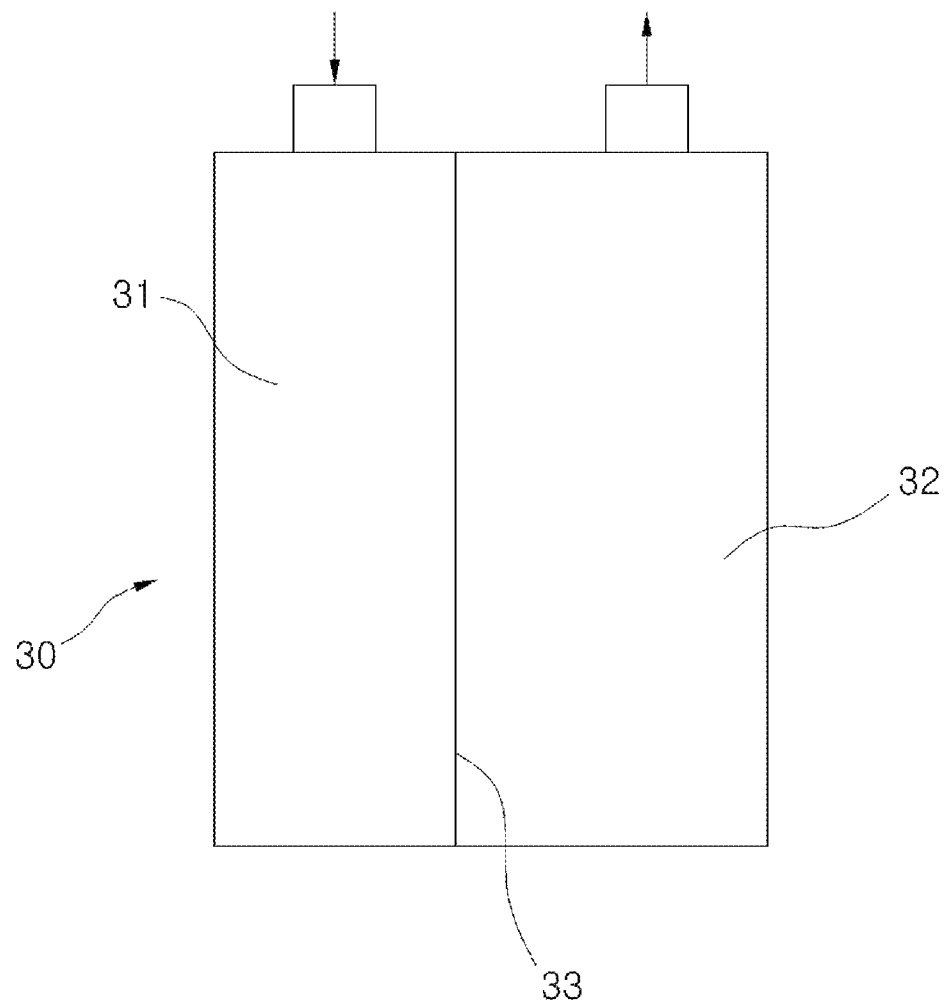
FIG. 5 is a diagram illustrating a cleansing solution providing member according to an embodiment of the present invention.
Figure 6:
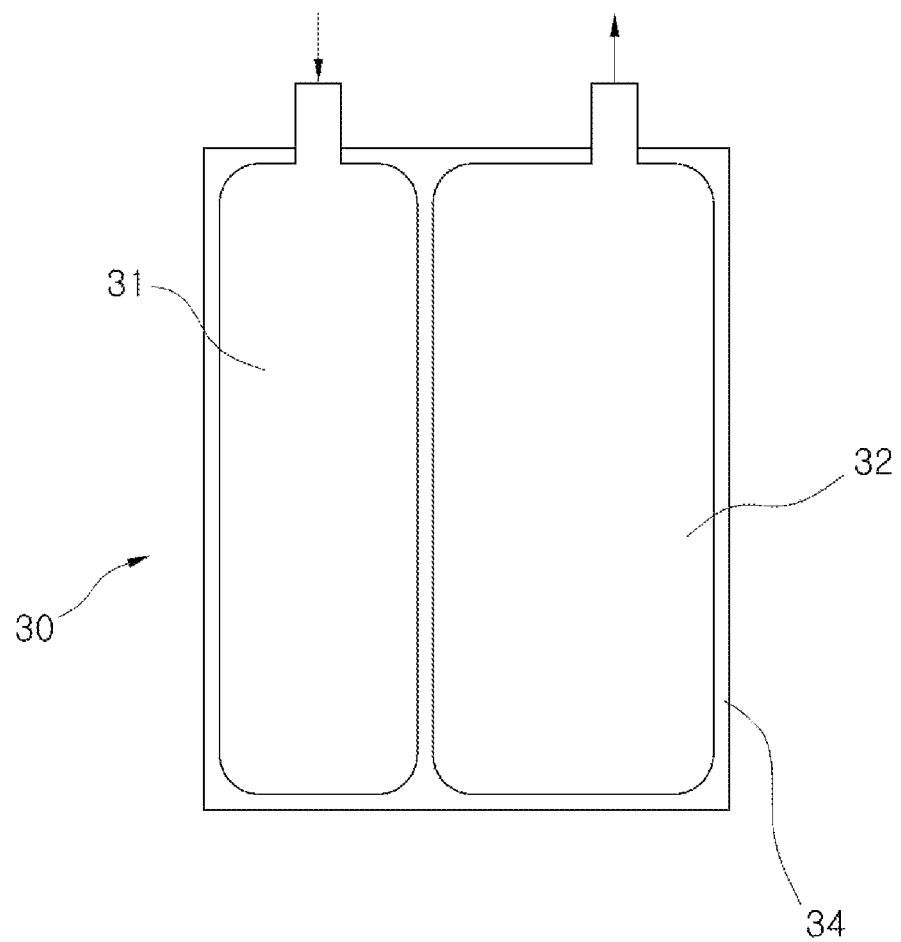
FIG. 6 is a diagram illustrating another example of a cleansing solution providing member according to an embodiment of the present invention.

As shown in FIGS. 1 to 6, a colonic irrigator according to an embodiment of the present invention includes a cleansing body 10 having a laid down egg shape, which has a spray hole 12 formed at a lifted portion 11 provided on the upper part thereof and has a cleansing solution channel 13 formed therein to communicate with the spray hole 12, and a connector 20 which has a screw part 21 formed at one side thereof so as to be connected to a shower hose 40, is bent at 90 degrees such that the other side is connected to the lower part of the cleansing body 10, and has a cleansing solution channel 23 formed therein to communicate with the cleansing solution channel 13 of the cleansing body 10, wherein the cleansing body 10 and the connector 20 are integrated.

A water pressure regulating member that regulates the pressure of the cleansing solution sprayed through the spray hole 12 is provided at a side of the cleansing body 10, and a filter 22 is provided inside the entrance of the connector 20 to remove impurities contained in the cleansing solution. In addition, a flow regulating valve 24 may be further provided downstream of the filter 22 to regulate the spraying amount of the cleansing solution by changing an opening of the cleansing solution channel 23.

The filter 22 may be a stainless steel mesh filter, but the shape and materials are not limited thereto as long as it removes impurities in the cleansing solution.

The water pressure regulating member includes a cylinder-shaped extension portion 15 extended from a longitudinal end of the cleansing body 10 and having a pressure regulating hole 16 at a side thereof, a pressure regulating channel 17 formed at the extension portion 15 and the cleansing body 10 to connect the cleansing solution channel 13 of the cleansing body 10 and the pressure regulating hole 16 formed at the extension portion 15, and a silicone band 18 connected to the extension portion 15 and regulating the opening of the pressure regulating hole 16.

In the meantime, when the shower hose 40 is too short to reach a toilet, the shower hose 40 may be connected with a connection hose 40' using a hose connection tip 45 having screw parts at opposite ends. For example, the shower hose 40 and the connection hose 40' are connected to each other by using the hose connection tip 45, thereby making the assembly longer, and the connection hose 40' may be then connected to the connector 20 of the cleansing body 10. As such, although the shower is distant from the toilet, the large intestine may be cleansed by the cleansing body 10.

In addition, when water discharged from the shower hose 40 cannot be used as the cleansing solution, the shower hose 40 and the connector 20 are not connected directly to each other. Instead, a cleansing solution providing member 30 may be disposed between the shower hose 40 and the connector 20 to supply the cleansing solution to the connector 20 by using the pressure of water provided through the shower hose 40. In more detail, when tap water that is not potable, e.g., limewater or African underground water, is supplied through the shower hose 40, the tap water cannot be used for the cleansing solution. Thus, the cleansing solution providing member may be used to utilize a cleansing solution which is unharmful to a human body.

The cleansing solution providing member 30 includes a pressurizing portion 31 which volume expands due to the water provided by the shower hose 40, and a cleansing solution storing portion 32 storing the cleansing solution therein, which volume decreases as the volume of the pressurizing portion 31 expands, such that the cleansing solution is supplied to the connector 20.

Here, the pressurizing portion 31 and the cleansing solution providing portion 32 may be formed integrally using a container having a fixed volume, such as a plastic bag that is not stretchable. In this case, a flexible separating wall 33 may be disposed to partition the pressurizing portion 31 and the cleansing solution providing portion 32, thereby facilitating the maintenance therefor by reducing the number of components.

Also, the cleansing solution providing member 30 may have a structure in which the pressurizing portion 31 and the cleansing solution providing portion 32 are manufactured using an expandable container and stored in a sac 34 that has a predetermined volume.

The colonic irrigator according to an embodiment of the present invention cleanses the inside of large intestine using water supplied through the shower hose while being connected to the shower hose.

A shower head is detached from the shower hose and the connector 20 of the cleansing body 10 is then screwed to the shower hose. The lifted portion 11 disposed on an upper portion of the cleansing body 10 is inserted into a user's anus, which is followed by opening the cleansing solution channel 23 inside the connector 20 by regulating the flow regulating valve 24 provided at a side of the connector 20.

Accordingly, water provided through the shower hose 40 is sprayed into the anus through the spray hole 12 of the cleansing body 10, thereby cleansing the inside of the large intestine. However, since a single-time cleansing is insufficient to completely cleanse the large intestine, it is desirable to repeat the cleansing.

Since the cleansing body 10 has a laid down egg shape, it compresses a butt around the anus generating an inclination for stool and weakens the inclination for stool, thereby postponing a bowel movement. Thus, the amount of the cleansing solution supplied thereto increases and the cleansing solution can reach deeper into the anus.

In the meantime, when the water pressure sprayed through the spray hole 12 is too high or too low, the water pressure may be adjusted by regulating the opening of the pressure regulating hole 16 using the silicone band 18 disposed at the extension portion 15 formed in a side of the cleansing body 10. In this case, when the silicone band 18 increases the opening of the pressure regulating hole 16, the spraying pressure increases, whereas the silicone band 18 decreases the opening of the pressure regulating hole 16, the spraying pressure increases due to a negative pressure.

In addition, when the amount of water sprayed through the spray hole 12 is too large or too small, the opening of the cleansing solution channel 23 provided in the connector 20 may be adjusted by manipulating the flow regulating valve 24 so as to regulate the amount of water.

In case that the shower is distant from the toilet and the shower hose 40 cannot be assembled to the connector 20 at the toilet, the hose connection tip 45 may be used to connect the shower hose 40 and the connection hose 40', which is followed by connecting the connection hose 40' to the connector 20. Thus, it can be used regardless of the distance between the shower and the toilet.

Meanwhile, when tap water cannot be used, such as in a region where underground water is contaminated or tap water is limewater, the tap water cannot be used for the cleansing solution. In this case, a separate cleansing solution providing member 30 may be used.

The cleansing solution providing member 30 is disposed between the shower hose 40 and the connector 20 of the cleansing body 10. The shower hose 40 is connected to the pressurizing portion 31 of the cleansing solution providing member 30, and the cleansing solution storing portion 32 of the cleansing solution providing member 30 is connected to the connector 20 using, e.g., the connection hose 40', thereby allowing the cleansing solution of the cleansing solution storing portion 32 to be supplied into the cleansing body 10 through the connector 20 by means of the pressure of water provided through the shower hose 40. Accordingly, purified cleansing solution instead of the harmful water to a body is sprayed into the large intestine through the spray hole 12 of the cleansing body 10, thereby cleansing the large intestine.

Embodiments of technical spirit of the present invention is described and illustrated, but the present invention is not limited to the configurations and operations described in the embodiments. Rather, a person having ordinary skill in the art may understand that various other changes or modifications are possible without departing from the natural characteristics of the present invention described in the appended claims. Accordingly, all such modifications, enhancements, and other equivalents are intended to fall within the true scope of the present invention.

What is claimed is:

1. A colonic irrigator comprising:
   a cleansing body (10) having a laid down egg shape, having a spray hole (12) formed at a lifted portion (11) provided on the upper part thereof and having a cleansing solution channel (13) formed therein to communicate with the spray hole (12); and
   a connector (20) which has a screw part (21) formed at one side thereof so as to be connected to a shower hose (40), is bent at 90 degrees such that another side thereof is connected to a lower part of the cleansing body (10), and has a cleansing solution channel (23) formed therein to communicate with the cleansing solution channel (13) of the cleansing body (10),
   wherein the cleansing body (10) and the connector (20) are integrated, and
   wherein a water pressure regulating member is provided at a side of the cleansing body (10), wherein the water pressure regulating member comprises: a cylinder-shaped extension portion (15) extended from a longitudinal end of the cleansing body (10) and having a pressure regulating hole (16) at a side thereof; a pressure regulating channel (17) formed at the extension portion (15) and the cleansing body (10) to connect the cleansing solution channel (13) of the cleansing body (10) and the pressure regulating hole (16) formed at the extension portion (15), and a silicone band (18) connected to the extension portion (15) and regulating an opening of the pressure regulating hole (16).

2. A colonic irrigator comprising:
   a cleansing body (10) having a laid down egg shape, having a spray hole (12) formed at a lifted portion (11) provided on the upper part thereof and having a cleansing solution channel (13) formed therein to communicate with the spray hole (12); and
   a connector (20) which has a screw part (21) formed at one side thereof so as to be connected to a shower hose (40), is bent at 90 degrees such that another side thereof is connected to a lower part of the cleansing body (10), and has a cleansing solution channel (23) formed therein to communicate with the cleansing solution channel (13) of the cleansing body (10),
   wherein the cleansing body (10) and the connector (20) are integrated, and
   wherein a filter (22) is provided inside the entrance of the connector (20) to remove impurities contained in the cleansing solution and a flow regulating valve (24) is provided downstream of the filter (22) to regulate a spraying amount of the cleansing solution by changing an opening of the cleansing solution channel (23).

3. A colonic irrigator comprising:
   a cleansing body (10) having a laid down egg shape, having a spray hole (12) formed at a lifted portion (11) provided on the upper part thereof and having a cleansing solution channel (13) formed therein to communicate with the spray hole (12);
   a connector (20) which has a screw part (21) formed at one side thereof so as to be connected to a shower hose (40), is bent at 90 degrees such that another side thereof is connected to a lower part of the cleansing body (10), and has a cleansing solution channel (23) formed therein to communicate with the cleansing solution channel (13) of the cleansing body (10); and
   a hose connection tip (45) having screw parts at opposite ends to connect the shower hose (40) and a connection hose (40') when the shower hose (40) is short,
   wherein the cleansing body (10) and the connector (20) are integrated.

4. The colonic irrigator of claim 1, further comprising a cleansing solution providing member (30) disposed between the shower hose (40) and the connector (20) to supply the cleansing solution to the connector (20) due to the pressure of water provided through the shower hose (40), wherein the cleansing solution providing member (30) comprises: a pressurizing portion (31) which volume expands due to water provided by the shower hose (40); and a cleansing solution storing portion (32) storing the cleansing solution therein, which volume decreases as the volume of the pressurizing portion (31) expands, such that the cleansing solution is supplied to the connector 20.

5. The colonic irrigator of claim 4, wherein the pressurizing portion (31) and the cleansing solution providing portion (32) are integrally formed and partitioned by a flexible separating wall (33) disposed in a container having a predetermined volume.

6. The colonic irrigator of claim 1, further comprising a cleansing solution providing member (30) disposed between the shower hose (40) and the connector (20) to supply the cleansing solution to the connector (20) due to the pressure of water provided through the shower hose (40), wherein the cleansing solution providing member (30) comprises: a pressurizing portion (31) which volume expands due to water provided by the shower hose (40); and a cleansing solution storing portion (32) storing the cleansing solution therein, which volume decreases as the volume of the pressurizing portion (31) expands, such that the cleansing solution is supplied to the connector 20.

7. The colonic irrigator of claim 2, further comprising a cleansing solution providing member (30) disposed between the shower hose (40) and the connector (20) to supply the cleansing solution to the connector (20) due to the pressure of water provided through the shower hose (40), wherein the cleansing solution providing member (30) comprises: a pressurizing portion (31) which volume expands due to water provided by the shower hose (40); and a cleansing solution storing portion (32) storing the cleansing solution therein, which volume decreases as the volume of the pressurizing portion (31) expands, such that the cleansing solution is supplied to the connector 20.

8. The colonic irrigator of claim 3, further comprising a cleansing solution providing member (30) disposed between the shower hose (40) and the connector (20) to supply the cleansing solution to the connector (20) due to the pressure of water provided through the shower hose (40), wherein the cleansing solution providing member (30) comprises: a pressurizing portion (31) which volume expands due to water provided by the shower hose (40); and a cleansing solution storing portion (32) storing the cleansing solution therein, which volume decreases as the volume of the pressurizing portion (31) expands, such that the cleansing solution is supplied to the connector 20.

9. The colonic irrigator of claim 6, wherein the pressurizing portion (31) and the cleansing solution providing portion (32) are integrally formed and partitioned by a flexible separating wall (33) disposed in a container having a predetermined volume.

10. The colonic irrigator of claim 7, wherein the pressurizing portion (31) and the cleansing solution providing portion (32) are integrally formed and partitioned by a flexible separating wall (33) disposed in a container having a predetermined volume.

11. The colonic irrigator of claim 8, wherein the pressurizing portion (31) and the cleansing solution providing portion (32) are integrally formed and partitioned by a flexible separating wall (33) disposed in a container having a predetermined volume.

* * * * *